（12）United States Patent
Brown et al.

(10) Patent No.: US 8,467,494 B2
(45) Date of Patent: Jun. 18, 2013

(54) CONE BEAM Z-AXIS COVERAGE

(75) Inventors: Kevin M. Brown, Mentor on the Lake, OH (US); Dominic J. Heuscher, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 174 days.

(21) Appl. No.: 13/127,241

(22) PCT Filed: Oct. 28, 2009

(86) PCT No.: PCT/IB2009/054790
§ 371 (c)(1),
(2), (4) Date: May 3, 2011

(87) PCT Pub. No.: WO2010/052614
PCT Pub. Date: May 14, 2010

(65) Prior Publication Data
US 2011/0211664 A1 Sep. 1, 2011

Related U.S. Application Data

(60) Provisional application No. 61/112,291, filed on Nov. 7, 2008.

(51) Int. Cl.
*A61B 6/03* (2006.01)
(52) U.S. Cl.
USPC ............................................................ 378/4
(58) Field of Classification Search
USPC .................. 378/4, 15, 19, 62, 147, 119, 137, 378/138
See application file for complete search history.

(56) References Cited

U.S. PATENT DOCUMENTS

| 6,330,299 | B1 | 12/2001 | Curtis et al. |
| 6,510,195 | B1 | 1/2003 | Chappo et al. |
| 7,340,030 | B2 | 3/2008 | Altman et al. |
| 2005/0152490 | A1 | 7/2005 | Shechter |
| 2008/0123816 | A1 | 5/2008 | Mori et al. |

FOREIGN PATENT DOCUMENTS

| GB | 2422759 A | 8/2006 |
| WO | 2004075118 A1 | 9/2004 |
| WO | 2005059592 A1 | 6/2005 |
| WO | 2008042564 A1 | 4/2008 |

OTHER PUBLICATIONS

Dixon, R. L., et al.; An improved analytical model for CT dose simulation with a new look at the theory of CT dose; 2005; Med. Phys.; 32(12)3712-3728.

(Continued)

*Primary Examiner* — Irakli Kiknadze

(57) ABSTRACT

An imaging system includes a radiation source (110) with an anode (202). The radiation source (110) rotates around an examination region (106) about a longitudinal axis (108) and emits radiation from a focal spot (206) on the anode (202). A source collimator (112) collimates the emitted radiation to produce a generally conically shaped radiation beam that traverses the examination region. The generally conically shaped radiation beam has an extended cone angle along the longitudinal axis that is greater than an effective maximum cone angle determined by an anode angle of the anode (202). A detector array (116) detects radiation that traverses the examination region and generates signals indicative thereof. A reconstructor (118) reconstructs the signals to generate volumetric image data indicative of the examination region.

25 Claims, 4 Drawing Sheets

OTHER PUBLICATIONS

Maltz, J. S., et al.; Algorithm for X-ray Scatter, Beam-Hardening, and Beam Profile Correction in Diagnostic (Kilovoltage) and Treatment (Megavoltage) Cone Beam CT; 2008; IEEE Trans. on Medical Imaging; 27(12)1791-1810.

Wang, G.-C., et al.; Calibration of a PEM Detector with Depth of Interaction Measurement; 2004; IEEE Trans. on Nuclear Science; 51(3)775-781.

though this application describes physical translation of the focal spot, the focal spot can also electronically translate along the z-axis, for example, through deflection of an electron beam.

CONE BEAM Z-AXIS COVERAGE

CROSS REFERENCE TO RELATED APPLICATION

This application claims benefit of U.S. provisional application Ser. No. 61/112,291 filed Nov. 7, 2008, which is incorporated herein by reference The following generally relates to cone beam computed tomography (CT). However, it is also amenable to other medical imaging applications and to non-medical imaging applications.

A cone-beam computed tomography (CT) scanner generally includes an x-ray tube and a two-dimensional detector array, which are affixed on a rotor on opposite sides of an examination region. The rotor is rotatably supported by a stationary frame and rotates about a longitudinal or z-axis around the examination region, thereby rotating the x-ray tube and the detector array about the longitudinal axis and around the examination region. The x-ray tube emits radiation, from a focal spot on an anode of the tube, that traverses the examination region and illuminates the detector array. A source collimator collimates the emitted radiation so that a generally cone-shaped radiation beam traverses the examination region. A patient support supports an object or subject in the examination region The angle of the cone beam along the longitudinal axis defines a z-axis width or scan coverage and has been referred to as the cone angle. Generally, the extent of the cone angle is limited by the heel effect, which is a function of the anode angle (e.g., typically eight degrees (8°)). Rays emanating from the side of the beam closer to the anode, with respect to a center ray of the beam, are attenuated and hardened relative to rays emanating from the side of beam closer to the cathode. As a consequence, the intensities of the rays on the anode side are less than the intensities of the rays on the cathode side, with the hardening and drop in intensity and an increase in the mean energy increasing as the angle increase in the direction of the anode. As a result, the anode angle generally defines an effective maximum cone angle in that the intensity and energy of rays for larger angles generally are not suitable for CT applications.

As such, the anode angle defines an effective maximum volume or z-axis coverage that can be scanned at any moment in time. Unfortunately, this volume may not be enough for certain scans, such as scans covering an entire organ such as the entire heart without having to translate the radiation beam or the patient in the z-axis direction. As a consequence, scan time may be increased and the resulting data for a whole organ scan may include motion artifact. With one CT scanner, an x-ray tube with a larger anode angle (e.g., twelve degrees (12°)) has been used to increase the effective maximum volume or z-axis coverage. However, increasing the anode angle also may reduce the focal spot size on the anode, the power rating of the x-ray tube and imaging resolution and increases cone beam artifact. Moreover, the z-axis scan coverage may still not be enough to cover an entire organ without having to translate the radiation beam or the patient in the z-axis direction.

Aspects of the present application address the above-referenced matters and others.

According to one aspect, a medical imaging system includes a radiation source with an anode. The radiation source rotates around an examination region about a longitudinal axis and emits radiation from a focal spot on the anode. A source collimator collimates the emitted radiation to produce a generally conically shaped radiation beam that traverses the examination region. The generally conically shaped radiation beam has an extended cone angle along the longitudinal axis that is greater than an effective maximum cone angle determined by an anode angle of the anode. A detector array detects radiation that traverses the examination region and generates signals indicative thereof. A reconstructor reconstructs the signals to generate volumetric image data indicative of the examination region.

According to another aspect, a method includes collimating a radiation beam emitted from a focal spot on an anode of a radiation source of an imaging system to produce a generally conically shaped radiation beam having an extended cone angle along a longitudinal axis that is greater than an effective maximum cone angle determined by an anode angle of the anode and acquiring projection data indicative of the radiation that traverses an examination region and illuminates a detector array.

According to another aspect, a computer readable storage medium is encoded with instructions which, when executed by a computer processor(s), cause the computer processor(s) to provide a control signal to position collimator blades of a collimator to collimate a radiation beam emitted from a focal spot on an anode of a radiation source of an imaging system to selectively produce a generally conically shaped radiation beam alternately having a symmetrically or asymmetrically extended cone angle along a longitudinal axis that is greater than an effective maximum cone angle determined by an anode angle of the anode.

The invention may take form in various components and arrangements of components, and in various steps and arrangements of steps. The drawings are only for purposes of illustrating the preferred embodiments and are not to be construed as limiting the invention.

Figure 1:
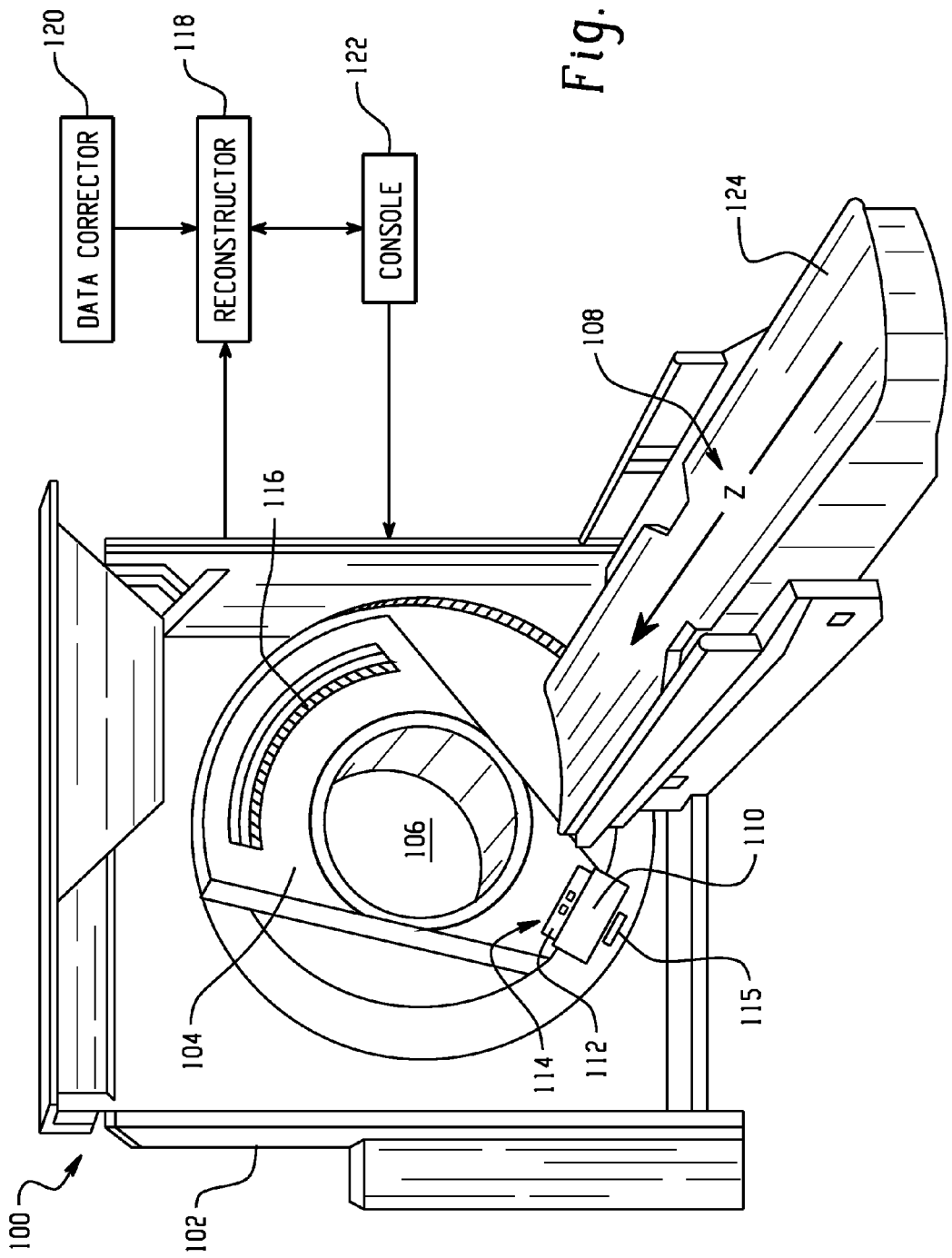
FIG. 1 illustrates an example imaging system.

FIG. 1 illustrates an imaging system 100 such as a computed tomography scanner. The imaging system 100 includes a stationary gantry 102, which remains generally stationary during scanning, although it can be configured to tilt and/or otherwise be moved. The system 100 also includes a rotating gantry 104, which is rotatably supported by the stationary gantry 102 via a bearing or the like. The rotating gantry 104 is configured to rotate around an examination region 106 about a longitudinal or z-axis 108.

The rotating gantry 104 supports a radiation source 110, such as an x-ray tube. In the illustrated embodiment, the radiation source 110 includes an eight degree (8°) anode (not visible) and emits radiation from a focal spot (not visible) thereon. The emitted radiation traverses the examination region 106 and any object or subject dispose therein. The focal spot emits radiation while the rotating gantry 104, and hence the radiation source 110 and the focal spot, rotate around the z-axis 108 during a helical or axial scan or are at a static position for a pilot or scout scan.

In the illustrated embodiment, the focal spot can translate along the z-axis physically, for example, by translating the radiation source 110 along the z-axis, and/or electronically. In one non-limiting instance, the focal spot translates in coordination with motion of an object such as an organ like the heart disposed within the examination region 106 or a flow of a contrast agent or the like through an object disposed within the examination region 106. Such coordination can be in connection with fly-by scanning in which the radiation source 110 physically translates along the z-axis 108. Examples of such scanning are discussed at least in patent application serial no. PCT/US07/78130, filed Sep. 11, 2007, and entitled "Fly-By Scanning," which is incorporated herein in its entirety by reference.

A source collimator 112 translates in coordination with the radiation source 110 and collimates the emitted radiation in the z-axis direction to produce a generally conical shaped radiation beam that traverses the examination region 106. In other embodiments, the collimator 112 is used to produce a generally fan, wedge or otherwise shaped radiation beam. The collimator 112 includes at least one collimator blade 114 configured to translate in the z-axis direction, relative to the radiation source 110. The illustrated scanner 100 includes N collimator blades 114, wherein N is two (2). In other embodiments, N can be more or less than two (2).

In the illustrated embodiment, the source collimator 112 is employed to produce a cone beam, which has a cone angle along the z-axis that defines the z-axis width or scan coverage. As described in greater detail below, in one instance the source collimator 112 increases the effective maximum cone-beam angle in both directions along the z-axis. This may include symmetrically or asymmetrically increasing the cone beam angle in both directions along the z-axis about an imaginary axis that extends perpendicularly from the focal spot through a center region of the examination region 106 through the z-axis 108. It is to be appreciated that by increasing the cone beam angle as such, the z-axis coverage can be expanded while maintaining the same radiation source power, relative to a configuration where the cone beam angle is not increased beyond the effective maximum cone-beam angle, which generally is defined by the angle of the anode (not visible) of the radiation source 110.

A controller 115 controls the source collimator 112 based on a scan protocol, including, but not limited to, a fly by scan or other scan protocol, and/or otherwise.

The rotating gantry 104 also supports a radiation sensitive detector array 116, which is disposed about the rotating gantry portion 104 and subtends an angular arc opposite the radiation source 110. The detector array 116 includes a multi-slice detector having a plurality of detector elements extending in the axial and transverse directions. Each detector element detects radiation emitted by the radiation source 110 that traverses the examination region 106 for at least one hundred and eighty degrees (180°) plus a fan angle of data, and generates a corresponding output signal or projection data indicative of the detected radiation. A non-limiting example of a suitable detector includes a tile detector as are described in U.S. Pat. No. 6,510,195 B1 to Chappo et al., filed Jul. 18, 2001, and entitled "Solid State X-Radiation Detector Modules and Mosaics Thereof, and an Imaging Method and Apparatus Employing the Same," which is incorporated herein in its entirety by reference.

A one or two dimensional anti-scatter grid may be employed in connection with the detector array 116 to mitigate or reduce detection of scatter radiation.

The projection data generated by the detector array 116 are conveyed to a reconstructor 118, which reconstructs the projections and generates volumetric image data. The image data can be processed by an image processor to generate one or more images of the scanned region of interest or a subset thereof.

A data corrector 120 can be used to correct the data for reconstruction. In one instance, this includes applying a correction that reduces the heel effect by providing a correction for increased attenuation and/or beam hardening. Such a correction may be used when the employed cone beam angle exceeds the effective maximum cone beam angle, as defined by the anode angle. As the heel effect varies along the z-axis, the correction may vary along the z-axis, with the largest correction generally being applied to the end ray(s) on the heel side of the cone beam.

An operator console 122 facilitates user interaction with the imaging system 100. Software applications executed by the operator console 122 allow the user to configure and/or control operation of the imaging system 100. For instance, the user can interact with the operator console 122 to select a fly-by or other scan protocol, and initiate, pause and/or terminate a scan, etc.

A couch or patient support 124 supports an object or subject such as a human or animal within the examination region 106. The support 124 can be movable, which enables an operator or the system to suitably position the object or subject within the examination region 106 before, during and/or after scanning.

The above system 100 can be employed for various applications. By way of non-limiting example, the system 100 is suited for whole organ scanning, such as scanning the entire heart or a substantial portion thereof in a single heart beat, if desired. Such a scan may be a fly-by or other scan performed with a radiation source having an eight degree (8°) or other angle anode, using full radiation source power for coverage between eight (8) to forty (40) centimeters (cm), such as 8 cm, 9 cm, 10 cm, 11 cm, 12 cm, etc. scans with minimal to substantially no motion artifacts and minimal to substantially no cone beam artifacts. With a fly-by scan, sufficient coverage can be obtained without sacrificing power and image quality.

Figure 2:
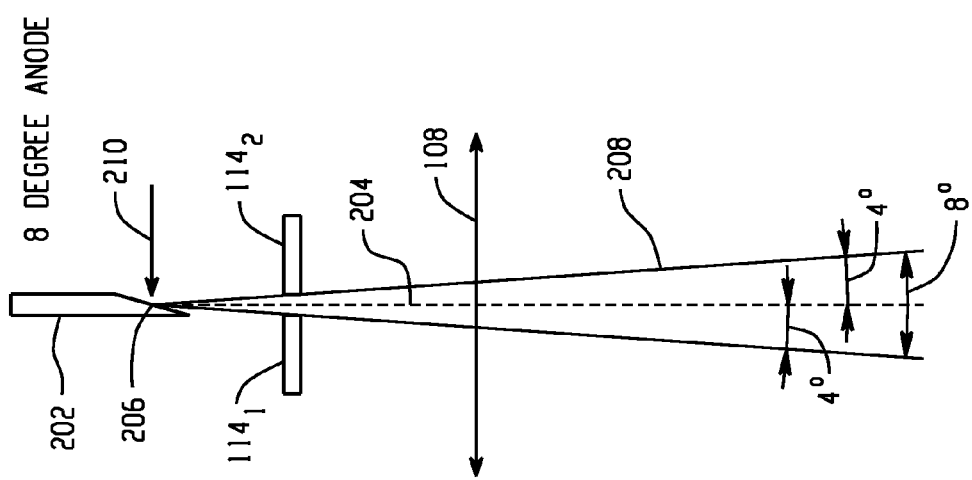
FIG. 2 illustrates a symmetric cone beam having an effective maximum cone angle based on the anode angle.

As briefly discussed above, the illustrated radiation source 110 can include an eight degree (8°) anode. FIG. 2 illustrates such an anode 202 in connection with collimator blades $114_1$ and $114_2$. As shown, the collimator blades $114_1$ and $114_2$ are opened to form a cone angle of eight degrees (8°), with a magnitude of four (4) degrees on each side of an axis 204, which extends perpendicularly from a focal spot 206 through the z-axis 108. With such a configuration, in one non-limiting example, the detector array 116 includes one hundred and twenty eight (128) rows of detector pixels along the z-axis 108, where each pixel is about 0.625 mm. Of course, more or less rows and/or other size pixels can be used in other embodiments.

Generally, the anode angle defines an effective maximum cone angle of a cone beam 208 that is symmetric about the axis 204, as the heel effect attenuates and hardens beam rays emanating from the focal spot 206 on the anode side of the axis 204 when the cone angle is greater than the effective maximum cone angle. As the cone angle increases beyond the effective maximum cone angle, the intensity of the rays substantially falls off and the rays are substantially attenuated such that the intensity and energy of the rays generally are not effective for CT applications. Such data does not render diagnostic data while still irradiating the patient. For an eight (8) degree anode angle, this angle is about eight degrees (8°), or four degrees (4°) on each side of the axis 204.

As shown in FIG. 2, the collimator blades 114 can be positioned to substantially or completely collimate rays emanating from the focal spot 206 at an angle greater than the effective maximum cone angle. With the anode 202 having an eight degree (8°) anode angle, the radiation source 110 can be operated at full power, with local heating from an electron beam 210 spread about the anode 202 as the anode 202 rotates and spread radially along the anode 202 slope. With this configuration, the effective focal spot size, as seen at the detector array 116, is small enough so as to maintain a suitable resolution along the z-axis, while providing suitable z-axis coverage and maximizing radiation source power.

Figure 3:
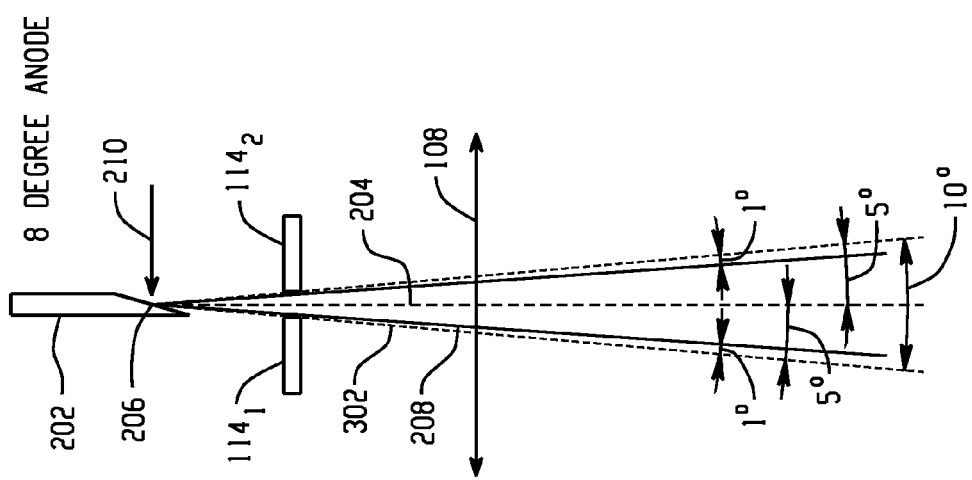
FIG. 3 illustrates an expanded symmetric cone beam having a cone angle that is larger than the effective maximum angle while maintaining the same tube power.

As shown in FIG. 3, the collimator blades $114_1$ and $114_2$ of the system 100 can be symmetrically opened to allow for a larger angle cone beam. In this example, the collimator blades $114_1$ and $114_2$ are opened to increase the cone angle from eight degrees (8°), as shown in FIG. 2, to about ten degrees (10°), with five degrees (5°) on each side of the axis 204. Relative to the configuration shown in FIG. 2, a resulting beam 302 has an expanded width along the z-axis, allowing for more rows of detector pixels, such as, for example, one hundred and sixty (160) rows of detector pixels, where each pixel is about 0.625 mm.

Note that the beam gets harder on the heel side and that a heel correction is applied to compensate for this hardening. As such, helical cone beam scans with extended z-axis coverage, for example, up to ten centimeters (10 cm), can be performed while maintaining radiation source power, without introducing significantly greater cone beam artifacts and/or decreasing resolution. Moreover, scan time and/or motion artifacts can be reduced. Similarly, more or less rows and/or other size pixels can be used in other embodiments. With the system of FIG. 2, the coverage is smaller, and with a system with a larger anode angle so as to achieve 10 cm of coverage, tube power must reduced, which may reduce image quality.

Figure 4:
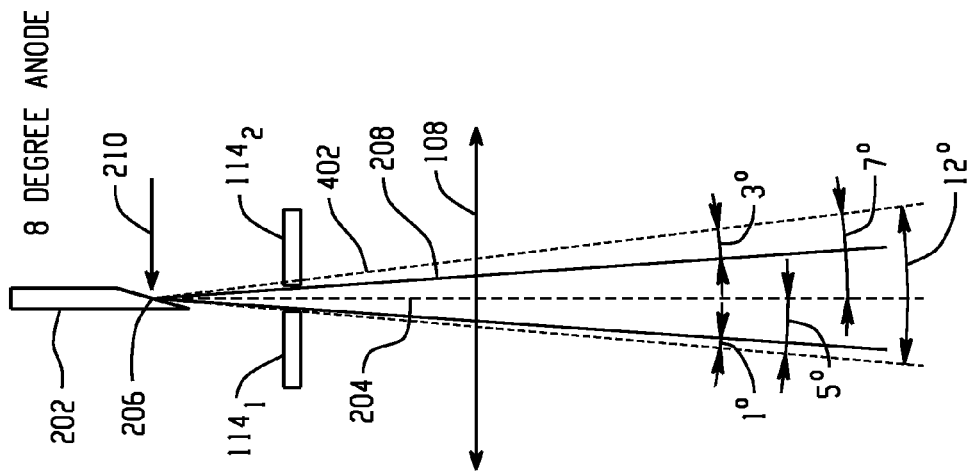
FIG. 4 illustrates an expanded asymmetric cone beam having a cone angle that is larger than the effective maximum angle while maintaining the same tube power.

As shown in FIG. 4, the collimator blades $114_1$ and $114_2$ are asymmetrically opened to allow for a larger angle cone beam. In this example, the collimator blades $114_1$ and $114_2$ are asymmetrically opened to increase the cone angle from eight degrees (8°), as shown in FIG. 2, to twelve degrees (12°), with five degrees (5°) on the heel side of the axis 204 and seven degrees (7°) on the other side of the axis 204. Again, relative to the configuration shown in FIG. 2, a resulting beam 402 has an expanded width along the z-axis, allowing for more rows of detector pixels, such as, for example, one hundred and ninety-two (192) rows of detector pixels, where each pixel is about 0.625 mm.

As such, helical cone beam scans with extended z-axis coverage, for example, up to twelve centimeters (12 cm), can be performed while maintaining radiation source power, without significantly increasing cone beam artifacts and/or decreasing resolution, and possibly reducing scan time and/or motion artifacts. Note that with this configuration, the extended cone beam provides fifty percent (50%) more coverage for the same radiation source power used in connection with the embodiment of FIG. 2. Again, more or less rows and/or other size pixels can be used in other embodiments. In addition, with the system of FIG. 2, the coverage is smaller, and with a system with a larger anode angle so as to achieve 12 cm of coverage, tube power must reduced, which may reduce image quality.

In another embodiment, only the collimator blade $114_1$ on the anode 202 side is opened to increase the cone beam angle larger then the effective maximum cone beam angle as determined by the heel effect and anode angle. The collimator blade $114_1$ may be opened from one (1) to three (3) centimeters. Again, relative to the configuration shown in FIG. 2, the resulting beam has an expanded width along the z-axis. Furthermore, a beam hardening or heel correction is applied to compensate for beam hardening artifact.

The above system 100 can be employed for various applications. By way of non-limiting example, the system 100 is suited for whole organ scanning, such as scanning the entire heart or a substantial portion thereof in a single heart beat, if desired. Such a scan may be a fly-by or other scan performed with a radiation source having an eight degree (8°) or other angle anode, using full radiation source power for coverage between eight centimeters (8 cm) to forty centimeters (40 cm), such as 8 cm, 9 cm, 10 cm, 11 cm, 12 cm, etc. centimeters scans with minimal to substantially no motion artifacts and minimal to substantially no cone beam artifacts. With a fly-by scan, sufficient coverage can be obtained without sacrificing power and image quality.

They expanded coverage discussed above can be used with a fly-by scan. In such an instance, motion can be reduced relative to a configuration in which the cone beam angle is at most equal to the effective maximum cone angle as determined by the anode angle.

The above examples are provided for explanatory purposes and are not limiting. In other embodiments, radiation sources with larger or smaller anode angles and/or cone beams with larger or smaller symmetric or asymmetric cone angles are contemplated. For example, suitable anode angles range from seven (7) to twelve (12) degree angles correspond to suitable extended cone beam angles up to ten (10) to twenty (20) degree angles, etc.

Figure 5:
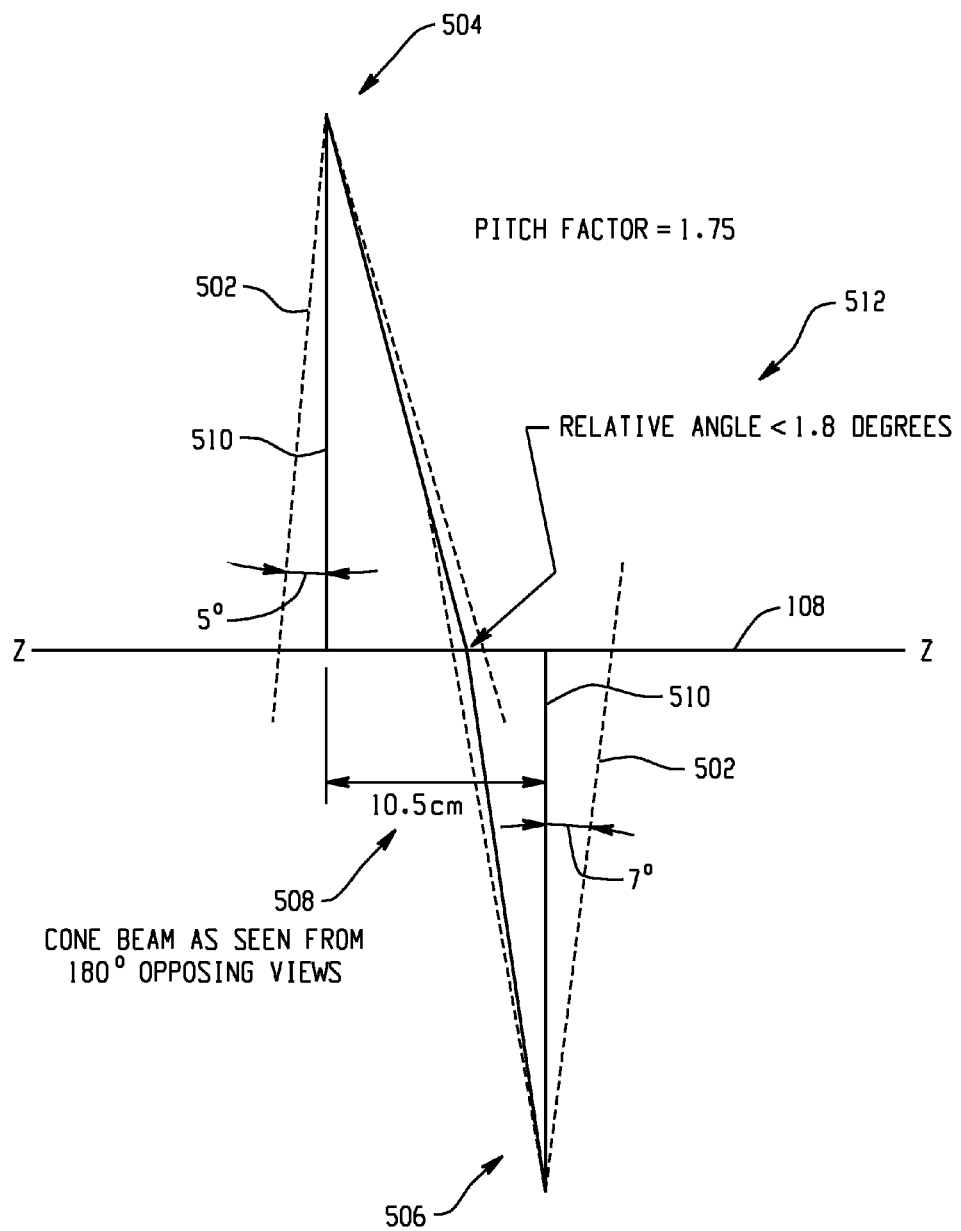
FIG. 5 illustrates the angle between opposing cone beam for an example helical scan.

The imaging system 100 can be used for various applications, including helical and/or axial scans. Generally, cone beam artifacts are smaller (e.g., less than twenty percent (20%)) for helical scans relative to axial scans, and for some helical scans, the cone beam artifacts are minimal. This is shown in connection with FIG. 5, which shows a cone beam 502 at a first position 504 and a second position 506, which is one hundred and eighty (180) degrees offset from the first position 504. The anode angle is eight degrees (8°) and the collimator blades 114 are positioned so that the cone beam has a twelve degree (12°) angle, as shown in connection with FIG. 4 above. The pitch factor is one and three quarters (1.75). With these parameters, a distance 508 between a ray 510 extending perpendicularly from a focal spot through the z-axis 108 at the positions 504, 506 is about ten and a half centimeters (10.5 cm), and a relative angle 512 between the beam 502 at the two positions 504, 506 is less than one and eight tenths degrees (1.8°).

Slice sensitivity is also generally more uniform for helical scans relative to axial scans. That is, for a given voxel in a helical reconstruction, the z-axis response will vary from about sixty percent (60%) of a nominal size to about one hundred and eighty-eight percent (188%) of the nominal size when the collimator blades 114 are positioned for a cone beam with an extended cone angle of twelve degrees (12°), as illustrated in FIG. 4. By way of example, with such a configuration, the size of a given voxel at the center of the cone will be about half a millimeter (0.5 mm), whereas the size of the voxel on the heel side of the axis 204 will be about three tenths of a millimeter (0.3 mm) and the size of the voxel on the other side of the axis will be about nine tenths of a millimeter (0.9 mm). The nominal size of the voxel will be the composite of the foregoing responses. As such, all voxels may have about the same nominal slice width sensitivity.

As noted herein, in one embodiment the collimator blades 114 can be positioned to increase z-axis coverage without reducing or sacrificing radiation source power or resolution or significantly increasing cone beam artifacts, noting that a heel effect correction may be performed on the data to correct for both increased attenuation and beam hardening, relative to an embodiment in which the collimator blades 114 are positioned based on the effective maximum cone angle defined by the anode angle, which assumes a maximum heel angle of 4 degrees for an 8 degree anode. A non-limiting suitable heel affect correction can be found in patent application WO/2005/059592, PCT/IB2002/052673, filed on Dec. 6, 2004, and entitled "CORRECTION OF ARTIFACTS CAUSED BY THE HEEL EFFECT," which is incorporated by reference, in its entirety, herein.

Figure 6:
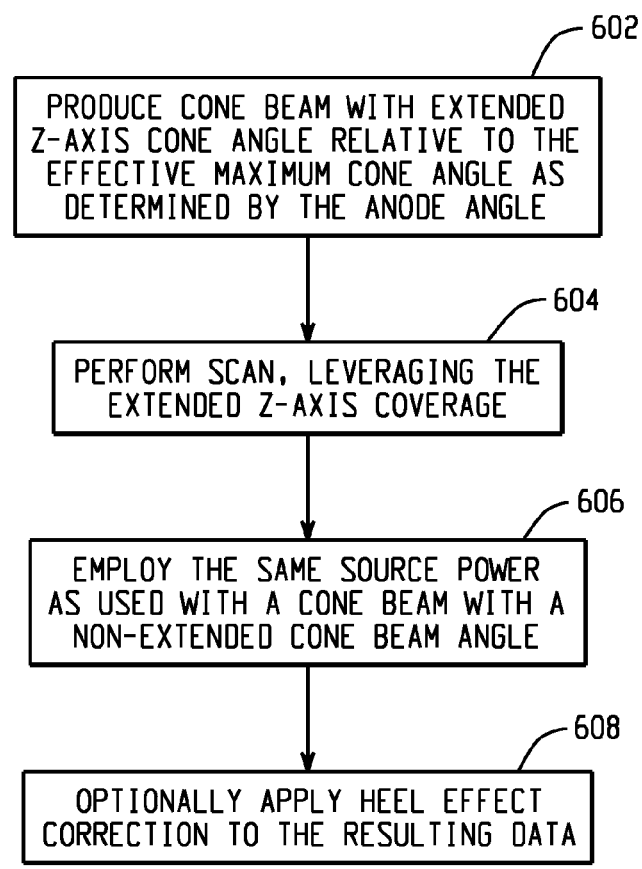
FIG. 6 illustrates an example method.

Example operation of the system 100 is discussed in connection with FIG. 6. It is to be appreciated that the order of the following acts is not limiting and may otherwise occur. In addition, more or less, including similar or different acts may be employed in other embodiments.

At 602, a cone beam having an extended cone angle along the z-axis and thus an extended z-axis scan coverage is produced. As discussed above, this may include symmetrically or asymmetrically opening the collimator blades 114 about the central ray axis 204 so as to produce a cone beam with a cone angle that is larger than the effective maximum cone angle determined by the anode angle.

At 604, a scan is performed with the cone beam. Such a scan may be a helical scan such as a fly by or other scan, an axial scan, and/or another scan. In addition, the scan can involve scanning an entire organ, such as a static or moving organ, without having to move or substantially move the radiation source 110 and/or the object or subject being scanned.

At 606, while performing the scan, the radiation source power is maintained at a power level such as full power as if the cone beam angle is not extended, but equal to the effective maximum cone beam angle. In one instance, this may be defined by $2(\alpha-4)$.

At 608, an optional heel effect correction is applied. Such a correction can be applied to the raw data, the reconstructed volumetric image data, and/or one or more images generated as part of the reconstructed volumetric image data.

The above may be implemented by way of computer readable instructions, which when executed by a computer processor(s), cause the processor(s) to carry out the foregoing. In such a case, the instructions are stored in a computer readable storage medium associated with or otherwise accessible to a relevant computer, such as a dedicated workstation, a home computer, a distributed computing system, the console, and/or other computer. The acts need not be performed concurrently with data acquisition.

The above may be used in various applications including applications where it may be desirable to achieve relatively large coverage in a relatively short period of time without moving the patient support such as for cardiac, trauma, perfusion and/or other applications.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention is claimed to be:

1. An imaging system, comprising:
a radiation source, including an anode, that rotates around an examination region about a longitudinal axis and emits radiation from a focal spot on the anode, wherein a power level of the radiation source is a same power level used with a cone angle that is about equal to the effective maximum cone angle determined by the heel effect, which is determined by an anode angle of the anode;
a source collimator that collimates the emitted radiation to produce a generally conically shaped radiation beam that traverses the examination region, wherein the generally conically shaped radiation beam has an extended cone angle along the longitudinal axis that is greater than an effective maximum cone angle determined by an anode angle of the anode;
a detector array that detects radiation that traverses the examination region and generates signals indicative thereof; and
a reconstructor that reconstructs the signals to generate volumetric image data indicative of the examination region.

2. The system of claim 1, wherein the extended cone angle is extended along the longitudinal axis in the anode direction.

3. The system of claim 1, wherein the extended cone angle is symmetrically extended in both directions along the longitudinal axis.

4. The system of claim 1, wherein the extended cone angle is asymmetrically extended in both directions along the longitudinal axis.

5. The system of claim 1, wherein the radiation source physically translates along the longitudinal axis during a fly-by scan.

6. The system of claim 1, further including a data corrector that corrects the signal for beam hardening corresponding to the heel side of the generally conically shaped radiation beam.

7. The system of claim 6, wherein the data corrector further corrects the signal for increased attenuation corresponding to the heel side of the generally conically shaped radiation beam.

8. The system of claim 1, wherein the effective maximum cone angle is about eight degrees and the extended cone angle is about ten to about twelve degrees.

9. The system of claim 8, wherein the extended cone angle is extended in the direction of the anode by about one degree and in the direction of the cathode by about one to about three degrees.

10. The system of claim 1, wherein the system performs a helical scan and at least two voxels have the same nominal slice width sensitivity.

11. The system of claim 1, wherein the anode angle is about eight degrees.

12. A method, comprising:
collimating a radiation beam emitted from a focal spot on an anode of a radiation source of an imaging system to produce a generally conically shaped radiation beam having an extended cone angle along a longitudinal axis that is greater than an effective maximum cone angle determined by an anode angle of the anode;
supplying a radiation source power at the same power level as used when the collimating the radiation to produce the generally conically shaped radiation beam with the effective maximum cone angle; and
acquiring projection data indicative of the radiation that traverses an examination region and illuminates a detector array.

13. The method of claim 12, further including symmetrically extending the cone angle in both directions along the longitudinal axis.

14. The method of claim 13, wherein the cone angle is extended by about one degree in each direction.

15. The method of claim 12, further including asymmetrically extending the cone angle in both directions along the longitudinal axis.

16. The method of claim 15, wherein the cone angle is extended by about one degree in a direction corresponding to the heel and by about one to three degrees in an opposing direction.

17. The method of claim 12, further including physically translating the radiation source along the longitudinal axis during a fly-by scan.

18. The method of claim 12, further including correcting the projection data for beam hardening corresponding to the heel effect.

19. The method of claim 12, further including correcting the projection data for attenuation corresponding to the heel effect.

20. A non-transitory computer readable medium encoded with computer readable instructions, which, when executed by a computer processor(s), causes the processor(s) to:
provide a control signal to position collimator blades of a collimator to collimate a radiation beam emitted from a focal spot on an anode of a radiation source of an imaging system to selectively produce a generally conically shaped radiation beam alternatively having a symmetrically or asymmetrically extended cone angle along a longitudinal axis that is greater than an effective maximum cone angle determined by an anode angle of the anode, a power level of the radiation source is a same power level used with a cone angle that is about equal to the effective maximum cone angle determined by the heel effect, which is determined by an anode angle of the anode.

21. An imaging system, comprising:
a radiation source, including an anode, that rotates around an examination region about a longitudinal axis and emits radiation from a focal spot on the anode, wherein the radiation source physically translates along the longitudinal axis during a fly-by scan;
a source collimator that collimates the emitted radiation to produce a generally conically shaped radiation beam that traverses the examination region, wherein the generally conically shaped radiation beam has an extended cone angle along the longitudinal axis that is greater than an effective maximum cone angle determined by an anode angle of the anode;
a detector array that detects radiation that traverses the examination region and generates signals indicative thereof; and
a reconstructor that reconstructs the signals to generate volumetric image data indicative of the examination region.

22. An imaging system, comprising:
a radiation source, including an anode, that rotates around an examination region about a longitudinal axis and emits radiation from a focal spot on the anode;
a source collimator that collimates the emitted radiation to produce a generally conically shaped radiation beam that traverses the examination region, wherein the generally conically shaped radiation beam has an extended cone angle along the longitudinal axis that is greater than an effective maximum cone angle determined by an anode angle of the anode;
a detector array that detects radiation that traverses the examination region and generates signals indicative thereof;
a data corrector that corrects the signals for beam hardening corresponding to the heel side of the generally conically shaped radiation beam; and
a reconstructor that reconstructs the corrected signals to generate volumetric image data indicative of the examination region.

23. A method, comprising:
physically translating a radiation source along a longitudinal axis during a fly-by scan;
collimating a radiation beam emitted from a focal spot on an anode of the radiation source of an imaging system to produce a generally conically shaped radiation beam having an extended cone angle along the longitudinal axis that is greater than an effective maximum cone angle determined by an anode angle of the anode; and
acquiring projection data indicative of the radiation that traverses an examination region and illuminates a detector array.

24. A method, comprising:
collimating a radiation beam emitted from a focal spot on an anode of a radiation source of an imaging system to produce a generally conically shaped radiation beam having an extended cone angle along a longitudinal axis that is greater than an effective maximum cone angle determined by an anode angle of the anode;
acquiring projection data indicative of the radiation that traverses an examination region and illuminates a detector array; and
correcting the projection data for beam hardening corresponding to the heel effect.

25. A method, comprising:
collimating a radiation beam emitted from a focal spot on an anode of a radiation source of an imaging system to produce a generally conically shaped radiation beam having an extended cone angle along a longitudinal axis that is greater than an effective maximum cone angle determined by an anode angle of the anode;
acquiring projection data indicative of the radiation that traverses an examination region and illuminates a detector array; and
correcting the projection data for attenuation corresponding to the heel effect.

* * * * *